United States Patent [19]
Leason et al.

[11] Patent Number: 5,857,843
[45] Date of Patent: Jan. 12, 1999

[54] PERISTALTIC PUMP WITH REMOVABLE ROTOR

[75] Inventors: John A. Leason, Norwell; Keith J. Jorgensen, Stoughton, both of Mass.

[73] Assignee: Harvest Technologies LLC, Norwell, Mass.

[21] Appl. No.: 733,913

[22] Filed: Oct. 18, 1996

Related U.S. Application Data

[60] Provisional application No. 60/008,127 Oct. 20, 1995 and provisional application No. 60/008,128 Oct. 20, 1995 and provisional application No. 60/005,772 Oct. 20, 1995.

[51] Int. Cl.⁶ ................................................. F04B 43/12
[52] U.S. Cl. .................................... 417/477.9; 417/477.1; 417/360
[58] Field of Search ........................... 417/477.9, 477.1, 417/238, 239, 360

[56] References Cited

U.S. PATENT DOCUMENTS

| | | | |
|---|---|---|---|
| 3,587,660 | 6/1971 | Dion | 139/84 |
| 4,527,323 | 7/1985 | Dawson | 29/451 |
| 4,631,008 | 12/1986 | Stenner | 417/477 |
| 4,813,855 | 3/1989 | Leveen et al. | 417/477 |
| 5,230,614 | 7/1993 | Zanger et al. | 417/477 |
| 5,257,917 | 11/1993 | Minarik et al. | 417/475 |
| 5,507,219 | 4/1996 | Stogner | 92/128 |

FOREIGN PATENT DOCUMENTS

| | | |
|---|---|---|
| 70.26869 | 2/1972 | France . |
| 593127 | 5/1959 | Italy . |

*Primary Examiner*—Timothy Thorpe
*Assistant Examiner*—Ehud Gartenberg
*Attorney, Agent, or Firm*—Dickinson Wright, PLLC

[57] ABSTRACT

A peristaltic pump has a rotor supported on a frame that is removable in a radial direction with respect to the axis of rotation of the rotor. The rotor is retained in place on the frame by gravity and the forces applied by the opposing pump components.

10 Claims, 1 Drawing Sheet

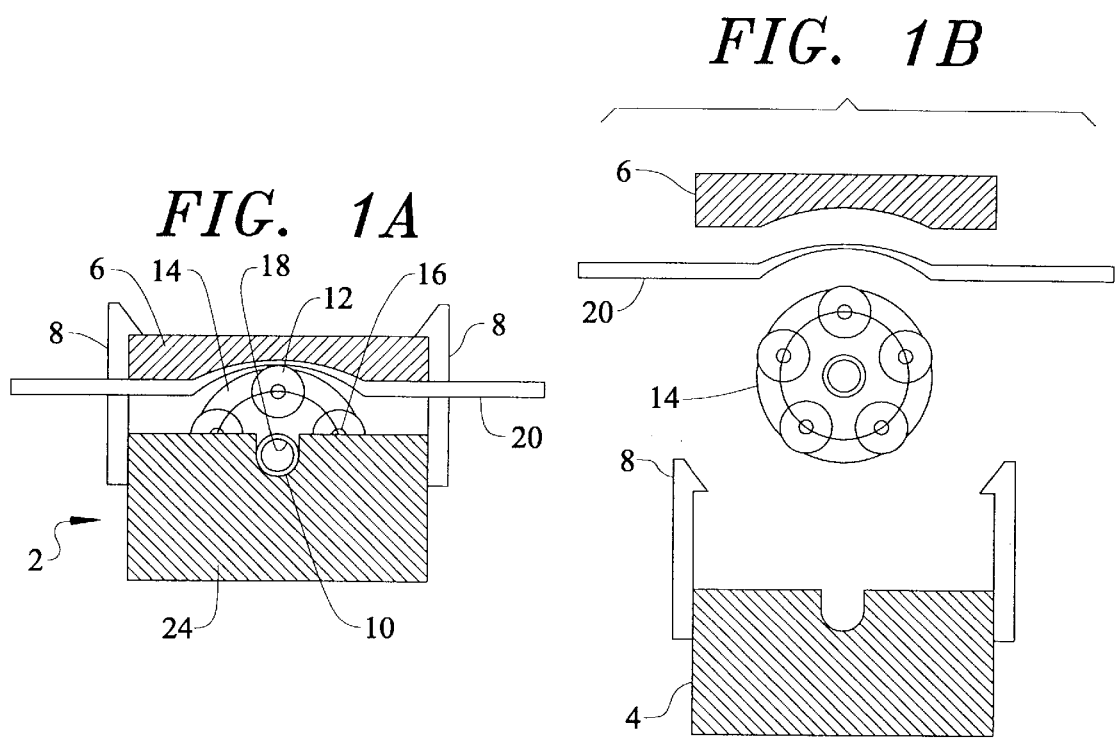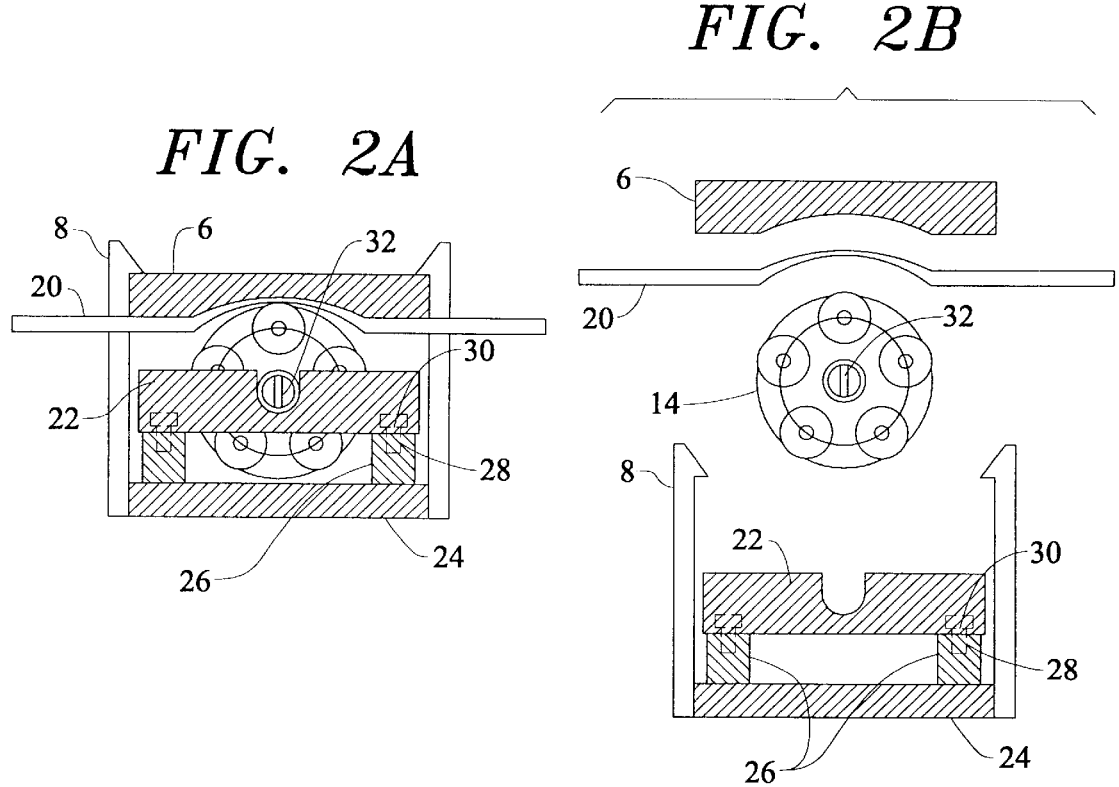

PERISTALTIC PUMP WITH REMOVABLE ROTOR

This application claims benefit of use Provisional Appl. Nos. 60/008,127 60/008,128, and 60/005,772 all filed Oct. 20, 1995.

TECHNICAL FIELD

This invention relates to the art of fluid pumps. In particular, the invention relates to the art of rotors used in peristaltic roller pumps.

BACKGROUND

Peristaltic pumps are commonly used in applications requiring the fluids being pumped to remain free of contamination or applications requiring the fluid path to remain clean or sterile. Such pumps must be disassembled regularly for cleaning or service, and it is desirable to be able to do so without tools. It is often difficult, however, to clean these pumps because the rotors are not easily removed.

SUMMARY OF THE INVENTION

In accordance with the invention a roller pump interfaces with a removable tube and platen. As with other peristaltic pumps, the rotor includes a frame with a number of rollers, which apply occlusive pressure against the tube. The platen resists the force applied by the rollers such that the tube is occluded as the rotor revolves. In the disclosed design, the platen may be removed by releasing a latching mechanism. The tube may then be removed, leaving the rotor free to be lifted out of the sub-frame.

In one use of the invention, the platen is formed into the bottom of a collection chamber used for the collection of fluids during surgery.

BRIEF DESCRIPTION OF THE INVENTION

FIGS. 1a and 1b are vertical cross sections of an embodiment of the invention with a solid frame.

FIGS. 2a and 2b are vertical cross sections of a second embodiment of the invention, where the frame includes elastic mounts.

DETAILED DESCRIPTION OF THE PREFERRED EMBODIMENTS

With reference to FIG. 1(a), a peristaltic pump 2 in accordance with the invention comprises a frame element 4 and a platen 6. The platen is removably attached to the frame by latches 8, such as spring loaded latches. The frame includes journals 10 for receiving the axle 12 of a rotor 14. The rotor includes one or more axle shafts 16 supporting the axle rollers. The axle shafts may include bushings or bearings to reduce rotational friction. The axle shafts rest on half-round journals 10, or bearing supports, which are an integral part of, or are attached to, the supporting pump frame 4. A tube 20 is placed between the rotor 14 and the platen 6 to carry fluid to be pumped. The tube will be occluded as the rotor rotates to pump the fluid.

Because the bearing supports are only half-round, the rotor may be installed or removed in a radial direction. Thus, as shown in FIG. 1(b), when the latches are released, the platen may be lifted from engagement with the rotor and the parts may be disassembled. The rotor is simply lifted from the frame for maintenance. The rotor may be installed simply by lowering it straight down, in a direction 90 degrees with respect to the axis of rotation of the axle 12.

During assembly, the rotor is first installed. The pump tube and platen are then installed and the platen latched to resist the force applied against it by the rotor. With the platen latched, the pump may operate in any orientation in a known manner.

It has been found through testing that it is desirable to allow the assembly to "flex" synchronously with the engagement of each roller against the platen as the rotor revolves. This desirable feature is provided in the embodiment shown in FIGS. 2(a) and 2(b). In accordance with this embodiment, the frame includes a main element 24 and a sub-frame 22. The sub-frame 22 is flexibly mounted to the pump frame by elastic mounts 26 to allow the sub-frame to move with respect to the main frame 24.

FIG. 2(b) shows the embodiment of FIG. 2(a) disassembled in a manner similar to that of FIG. 1(b).

In a further refinement of the invention, a threaded occlusion adjustment element 28 is provided in each of the elastic mounts. These adjustment elements are threaded rods that are secured to the elastic elements at one end and received in threaded blocks 30 in the sub-frame 22 at their opposed ends. Rotation of the threaded rods adjusts the height of the sub-frame with respect to the frame element 24. Thus the distance between the rotor 14 and the platen is adjusted. Other methods of allowing the assembly to "flex", such as flexibly mounting the platen, are possible.

The rotor shaft may be driven in any of several methods. Preferably, the rotor shaft is driven by a motor (not shown) having an output shaft aligned with the rotor shaft. The rotor shaft preferably includes a slot 32 extending completely across the diameter of the shaft for removable engagement with a flat tab on the end of the motor shaft. During removal of the rotor, the rotor shaft is rotated so that the slot is aligned with the radial direction of rotor removal, e.g., vertical, and the rotor is slid upward with respect to the motor shaft.

Modifications within the scope of the appended claims will be apparent to those of skill in the art.

We claim:

1. A peristaltic pump comprising a frame, a platen, means for attaching said platen to said frame, a tube for carrying a fluid to be pumped, and a rotor having an axle shaft extending long an axis, wherein said frame comprises means open on one side for receiving said axle shaft, allowing said rotor to rotate with respect to said platen about said axis, and allowing said rotor and said shaft to be separated from said frame by movement of said axle shaft in a direction transverse to said axis.

2. A peristaltic pump according to claim 1 wherein said means for receiving said axle shaft comprises at least one semi-circular bearing for engaging said axle shaft of said rotor and for allowing said axle shaft to be inserted into or removed from said bearing.

3. A peristaltic pump according to claim 2 wherein said means for attaching a platen to said frame provides a force on said rotor in said direction transverse to said axis to hold said axle shaft in said bearing during operation.

4. A peristaltic pump according to claim 1 wherein said frame comprises a first part resiliently attached to a second part, said means for receiving said axle shaft is in said first part and said means for attaching said platen is in said second part.

5. A peristaltic pump according to claim 1 wherein said axle shaft comprises drive means for removably connecting a drive motor to said shaft.

6. A peristaltic pump according to claim 5 wherein said drive means comprises a slot in said shaft, said slot extending in said direction transverse to said axis.

7. A peristaltic pump according to claim 1 wherein said platen is removable from said frame, and said means for attaching said platen allows said platen to be removed.

8. A peristaltic pump frame according to claim 1 wherein said frame comprises a first part resiliently attached to a second part, said means for supporting a rotor is in said first part, and said means for securing a platen is in said second part.

9. A peristaltic pump frame comprising means for supporting a rotor for rotation about an axis and means for securing a platen to said frame, wherein said means for supporting comprises means open on one side for receiving an axle shaft of sid rotor, allowing said rotor to rotate with respect to said frame about said axis, and allowing said rotor and said shaft to be separated from said frame by movement of said axle shaft in a direction transverse to said axis.

10. A peristaltic pump frame according to claim 9 wherein said means for securing a platen comprises a clip for removable attachment of said platen to said frame.

* * * * *